(12) United States Patent
Rudakov et al.

(10) Patent No.: US 6,371,980 B1
(45) Date of Patent: Apr. 16, 2002

(54) COMPOSITE EXPANDABLE DEVICE WITH IMPERVIOUS POLYMERIC COVERING AND BIOACTIVE COATING THEREON, DELIVERY APPARATUS AND METHOD

(75) Inventors: Leon V. Rudakov, Belmont; Mir A. Imran, Los Altos Hills; Linh Dinh, Santa Clara; Ara Davidian, Foster City; Kevin T. Larkin, Menlo Park, all of CA (US)

(73) Assignee: CardioVasc, Inc., Menlo Park, CA (US)

( * ) Notice: Subject to any disclaimer, the term of this patent is extended or adjusted under 35 U.S.C. 154(b) by 0 days.

(21) Appl. No.: 09/385,691

(22) Filed: Aug. 30, 1999

(51) Int. Cl.[7] ................................. A61F 2/06
(52) U.S. Cl. ................................. 623/1.12
(58) Field of Search ..................... 623/1.13, 415, 623/1.11, 1, 1.44, 1.46; 606/198, 194

(56) References Cited

U.S. PATENT DOCUMENTS

| | | | | |
|---|---|---|---|---|
| 5,653,747 A | * | 8/1997 | Dereume | ................ 623/1 |
| 5,667,523 A | * | 9/1997 | Bynon et al. | ............... 606/198 |
| 5,674,241 A | * | 10/1997 | Bley et al. | ................. 606/198 |
| 5,697,971 A | * | 12/1997 | Fischell et al. | ................ 623/1 |
| 5,843,117 A | * | 12/1998 | Alt et al. | ................... 606/194 |
| 5,911,754 A | * | 6/1999 | Kanesaka et al. | .............. 623/1 |
| 6,010,530 A | * | 1/2000 | Goicoechea | ................... 623/1 |
| 6,019,789 A | * | 2/2000 | Dinh et al. | .................... 623/1 |
| 6,022,374 A | * | 2/2000 | Imran | ............................ 623/1 |
| 6,066,167 A | * | 5/2000 | Lau et al. | ....................... 623/1 |
| 6,106,548 A | * | 8/2000 | Roubin et al. | ............. 623/1.15 |

* cited by examiner

*Primary Examiner*—Eduardo C. Robert
(74) *Attorney, Agent, or Firm*—Perkins Coie LLP; Peter J. Dehlinger; Larry W. Thrower

(57) ABSTRACT

A composite expandable device for delivery into a vessel carrying blood comprising an expandable support frame having first and second end portions. An impervious polymer sleeve having inner and outer surfaces extending over the support frame. A coating is disposed on at least one of the inner and outer surfaces of the polymer sleeve for enhancing endothelial cell growth on the device and polymer sleeve.

13 Claims, 3 Drawing Sheets

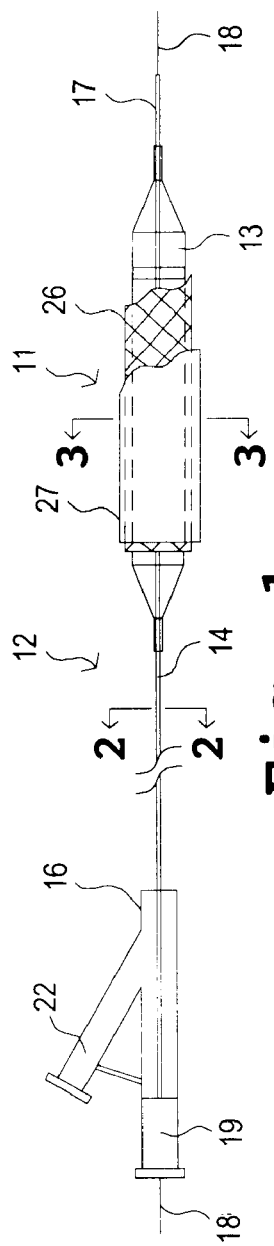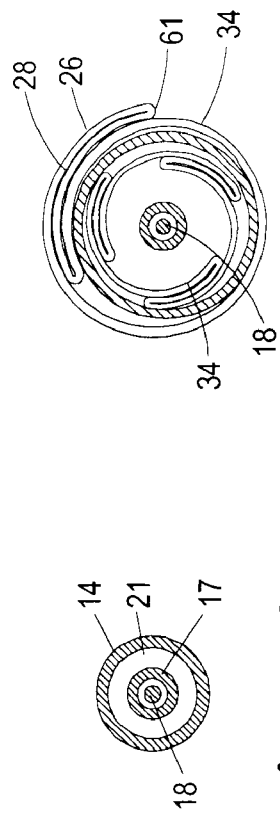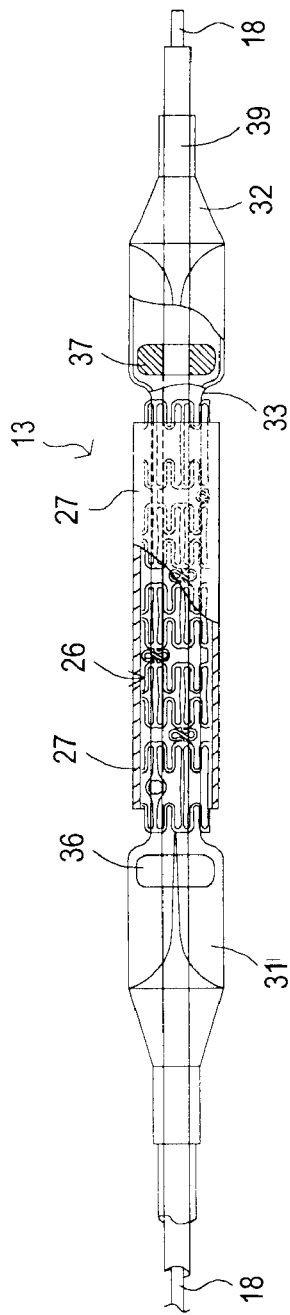

COMPOSITE EXPANDABLE DEVICE WITH IMPERVIOUS POLYMERIC COVERING AND BIOACTIVE COATING THEREON, DELIVERY APPARATUS AND METHOD

BACKGROUND OF THE INVENTION

This invention relates to a composite expandable device with a polymeric covering on the device and a bioactive coating on device and the polymeric covering, a delivery apparatus and a method.

Saphenous vein grafts have heretofore been utilized for bypassing occluded arterial blood vessels in the heart. Because they are vein tissue rather than arterial tissue, they have different characteristics and generally do not function well long term as arterial vessels. Saphenous bypass veins are less muscular and are generally quite flimsy and compliant. When these saphenous vein grafts become diseased with age, stenoses and obstructive deposits which are cheesy or buttery in consistency and which are very malleable are formed which cannot be treated effectively with interventional catheter procedures even when followed with a stent implant. The plaque material forming the stenosis tends to ooze through the stent struts and reoccludes flow passage through the stent and the saphenous vein graft. Other vascular obstructions, such as in femoral and popliteal vessels and in carotids as well as in native coronary arteries also suffer from occlusions. In many of these cases, plaque proliferates through the stents when stents are deployed in the vessels. Therefore a great need exits for a new and improved device and method to provide a lasting therapeutic relief in such situations.

SUMMARY OF INVENTION

In general, it is an object of the present invention to provide a composite expandable device with a substantially impervious polymeric covering thereon with a bioactive coating on the device and covering and a method for using the same which can be utilized for treating occlusions or partial occlusions in blood vessels and particularly saphenous vein grafts.

Another object of the invention is to provide a device of the above character which will provide a lasting therapeutic solution to the occurrence of plaque in stents in saphenous vein grafts.

Another object of the invention is to provide a device of the above character which can be used for repaving with endothelial cells the portion of the vessel being treated.

Another object of the invention is to provide a device of the above character which has physical characteristics which substantially match or mimic the physical characteristics of blood vessels.

Another object of the invention is to provide a device of the above character in which a uniformly distributed structural support is provided for the polymeric covering.

Another object of the invention is to provide a device of the above character which is very flexible and can bend axially to accommodate the tortuosity of blood vessels.

Another object of the invention is to provide a device of the above character which can be placed in tandem with another similar device in a vessel to treat a long stenosis in a vessel.

Additional objects and features of the invention will appear from the following description in which the preferred embodiments are set forth in detail in conjunction with the accompanying drawings.

BRIEF DESCRIPTION OF DRAWINGS

FIG. 1 is a side elevational view of a composite expandable device with a polymeric covering and a bioactive coating thereon, with certain portions broken away, mounted on a balloon delivery catheter.

FIG. 2 is a cross-sectional view taken along the line 2—2 of FIG. 1.

FIG. 3 is a cross-sectional view taken along the line 3—3 of FIG. 1.

FIG. 4 is an enlarged detail view of the balloon with the composite expandable device mounted thereon shown in FIG. 1.

DETAILED DESCRIPTION OF THE INVENTION

Figure 5:
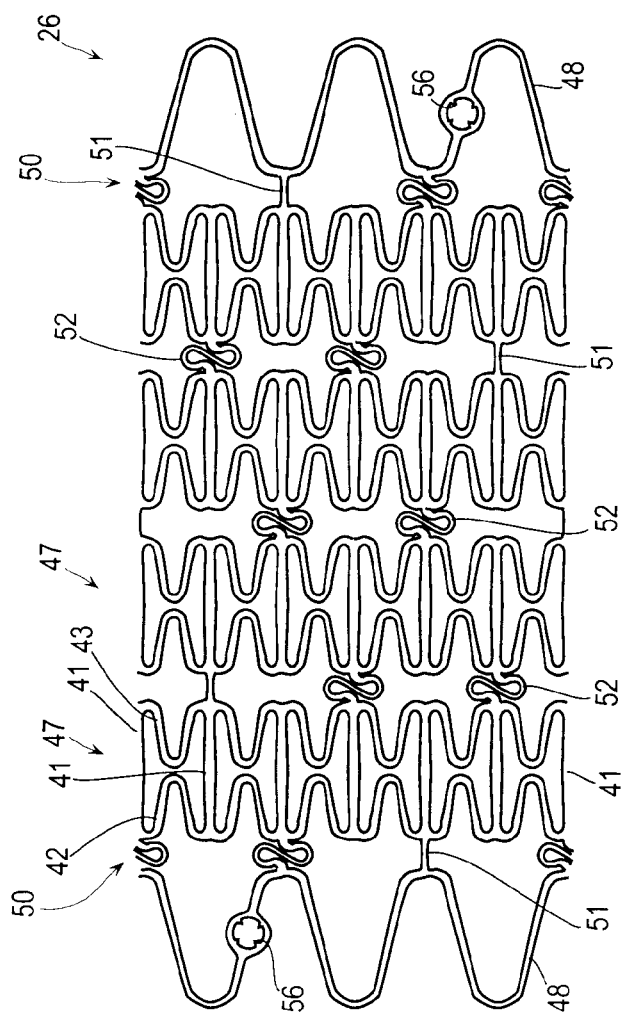
FIG. 5 is a plan view of the expandable device which has been split apart longitudinally and spread out to show its construction.

In general, the composite expandable device incorporating the present invention is for delivery into a vessel carrying blood and comprises an expandable support frame having first and second ends. An impervious polymer sleeve extends over the support frame and may leave the first and second ends of the support frame exposed. A bioactive coating is provided on one or both of the inner and outer surfaces of the polymer sleeve and the frame for enhancing endothelial cell growth on the blood contact surfaces of the polymer sleeve and frame.

More in particular, the composite expandable device 11 as shown is mounted on a delivery apparatus 12 which consists of an expandable balloon 13 mounted on the distal extremity of a shaft or catheter 14 and having a wye fitting 16 mounted on the proximal extremity. The shaft or catheter 14 is provided with a central lumen 17 which is adapted to receive a conventional guide wire 18 through a port 19 provided in the fitting 16. The catheter shaft 14 is provided with a concentric lumen 21 which is in communication with a port 22 of the fitting 16. The lumen 21 extends through the balloon 13 and an opening (not shown) is provided in the shaft 14 within the balloon for inflating and deflating the balloon.

The composite expandable device 11 consists of an expandable frame 26 which has a polymeric sleeve 27 covering the same. The sleeve has folds 28 therein when the frame is in an unexpanded condition as shown in FIG. 4.

The expandable balloon 13 has a substantially continuous diameter and is provided with distal and proximal portions 31 and 32 and an intermediate portion 33 which serves as a working portion of the balloon, having a length which will accept the length of the composite device 11. The balloon 13 is provided with folds 34 when deflated as shown in FIGS. 1, 3 and 4. Radiopaque marker bands 36 and 37 are provided on the portion of the shaft 14 extending through the balloon 13 and are mounted in the distal and proximal portions 31 and 32 as shown adjacent to the intermediate portion 33. These marker bands 36 and 37 are within the distal and proximal portions 31 and 32 of the balloon 13 but have a diameter which is substantially greater than the inner diameter of the intermediate portion 33 with the composite expandable device 11 mounted on the intermediate portion 33 to serve as stops or abutments to prevent the composite expandable device 11 from inadvertently slipping off of the balloon 13 during positioning and deployment of the composite expandable device 11.

The frame 26 which forms a part of the composite expandable device 11 consists of a plurality of circumferentially spaced-apart elongated struts 41 having first and second ends 42 and 43. Foldable links 46 are secured to the first and second ends 42 and 43 and extend circumferentially of the frame 26 and serve in conjunction with the elongate struts to form a circular belt 47. As shown in FIG. 4, a plurality of serially-connected belts 47 are provided which are axially aligned with each other.

Sinusoidal-shaped end portions 48 and 49 are provided on opposite ends of the plurality of serially-connected belts 47. Interconnecting means 50 is provided for interconnecting the plurality of belts 47 and the end portions 48 and 49 so that the belts 47 and end portions 48 and 49 extend along an axis while permitting axial bending between the belts 47 and the end portions 48 and 49 while maintaining a constant length of the device 11. The means 50 consists of at least one strut 51 which is relatively short in length in comparison to the length of the elongate struts 41 and a plurality of S-shaped links 52. Thus, as shown in FIG. 5, between each end portion and a belt and between adjacent belts there is provided a single strut 51 and two S-shaped links 52 all of which are spaced 120° apart the interconnecting means between adjacent belts and/or end portions are offset by 60°. Thus, with the construction shown in FIG. 4 there are provided four belts 47 and two end portions 48 and 49 with five sets of interconnecting means 50.

It can be seen that the length of the frame 26 can be readily increased or decreased by changing the number of belts 47 provided in the frame 26.

The frame 26 can be formed of a suitable material such as a metal or plastic. Suitable metals are stainless steel, titanium, and alloys thereof and other biocompatible metals. The plastic can be a polymer. Since the frame to be utilized in the composite expandable device is typically used in a saphenous vein graft, it need not have the radial strength normally required for stents placed in native arterial vessels. The frame 26 has been specifically designed to support the polymer sleeve 27 for use in a saphenous vein graft to closely approximate mechanical properties of the saphenous vein graft. The same principles can be used for a composite device for arterial vessels and other blood vessels. Thus the frame 26 provides the necessary strength and consistency throughout its length while giving good flexibility throughout its length to accommodate movement of the saphenous vein graft.

As shown in FIG. 4, the polymer sleeve extends over substantially the entire length of the frame 26 but leaving end portions 48 and 49 substantially exposed for a purpose hereinafter described. The sleeve 27 typically is formed of a suitable polymer. One polymer found to be particularly satisfactory is PTFE which is supplied as a tube having a wall thickness ranging from 0.002" to 0.010" and preferably 0.004" to 0.008" and having a suitable original diameter as for example 2 to 4.5 mm. The expanded PTFE material should have a pore size of approximately 10 to 50 μm. In addition in certain applications of this device, it may be desirable that the material be expandable from two to six times its original size yet retain elasticity properties to remain tightly over and in close engagement with the frame 26 prior to and after expansion. After placing the sleeve 27 over the working or intermediate portion 33 of the balloon, the sleeve 27 may be secured to the frame 26 so that it does not move axially of the frame 26 during deployment as hereinafter described. To accomplish this, the sleeve 27 can be wrapped into a fold or a wing 28 and held in place along a line 61 (see FIG. 3) or tacked by spaced-apart heat seals (not shown) that are easily rupturable upon expansion of the frame 26. It has been found that such tacking by the use of heat seals on a fold or wing of the polymer sleeve 27 makes it easy for the balloon 13 when expanding to open the sleeve 27 without any significant additional balloon pressure being required.

With such a construction as shown in FIG. 3, the frame 26 which has been crimped onto the intermediate portion 33 of the balloon 13 and the sleeve 27 wrapped over onto the same and seamed into place will have an overall profile which has a diameter or size which is not greater than or desirably less than the diameters of the proximal and distal portions 31 and 32. Since the marker bands 36 and 37 have larger diameters than the intermediate portion 33 of the balloon 13, they will ensure that the composite expandable device consisting of the frame 26 and the sleeve 27 cannot inadvertently slip off of the balloon 13 during the procedure.

Figure 6:
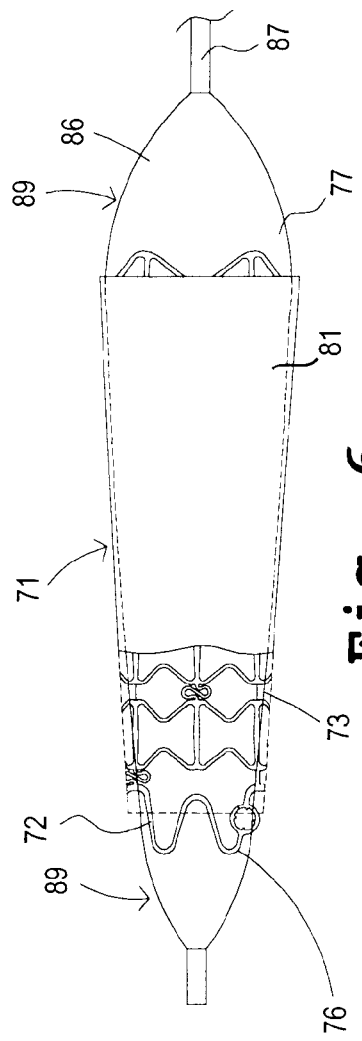
FIG. 6 is a side elevational view of another embodiment of a composite expandable device with polymeric covering and bioactive coating thereon which is tapered and is carried by a tapered balloon for expansion and delivery.
Figure 8:
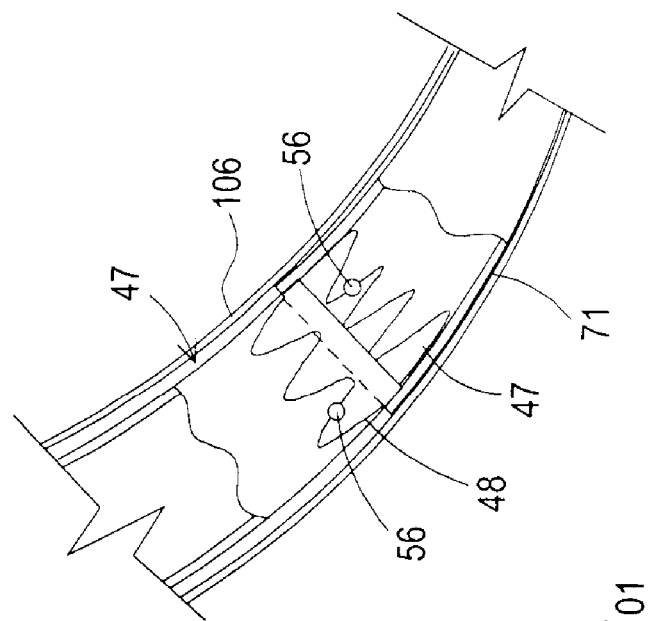
FIG. 8 is an enlarged detail view showing the docking of a tapered composite expandable device being docked with a cylindrical composite expandable device.
Figure 7:
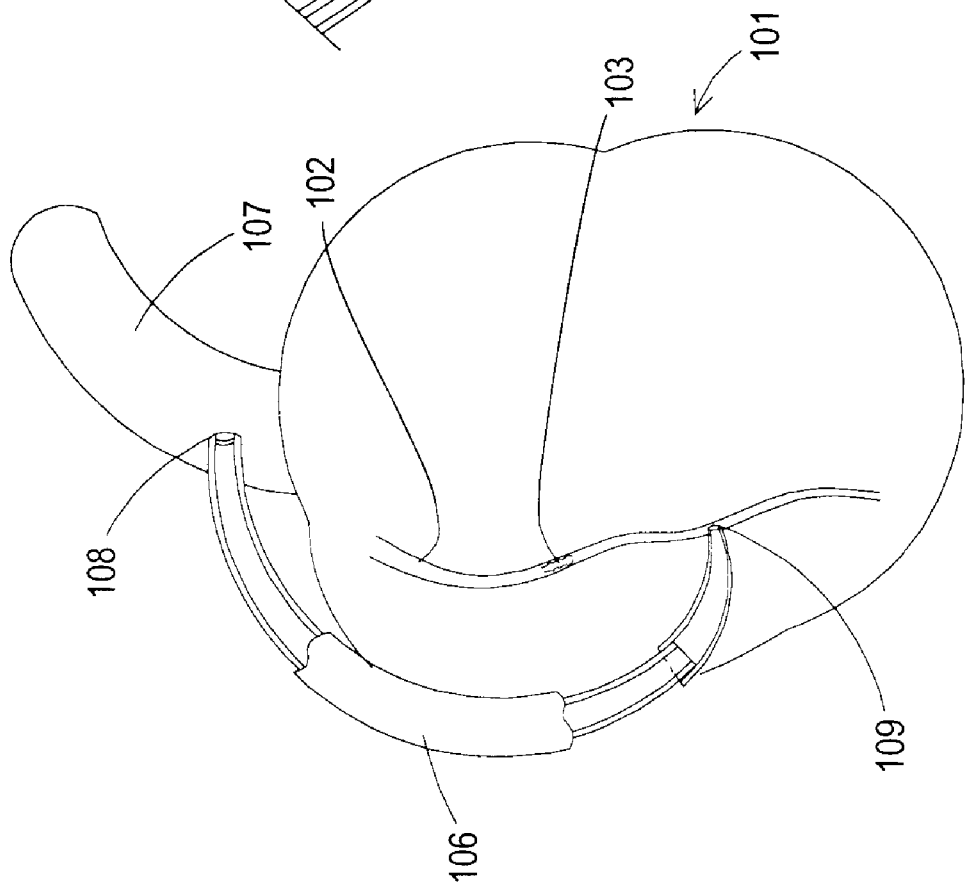
FIG. 7 is a schematic illustration of a heart showing the manner in which a saphenous vein graft is treated utilizing the composite expandable device of the present invention.

Another embodiment of a composite expandable device incorporating the invention is in the device 71 shown in FIG. 6. It is tapered rather than cylindrical to more closely approximate natural vessel geometry. In this device 71, a frame 72 is provided which is constructed in substantially the same manner as frame 26 but with the belts 73 increasing successively in circumference in one direction along the axis of the device 71 by providing foldable links 46 of successively greater lengths to provide the tapered construction shown in which one expandable end portion 76 has a lesser diameter than the other end portion 77. The means connecting the belts 73 and the end portions 76 and 77 are like the interconnecting means 50 hereinbefore described.

A tapered polymer sleeve 81 is provided on the exterior of the frame 72 while leaving the end portions 76 and 77 substantially exposed. A tapered balloon 86 is disposed within the frame 72 and is utilized for expanding the composite expandable device 71. The tapered balloon 86 is mounted on the distal extremity of a balloon shaft or catheter 87 and is constructed in the same manner as balloon shaft 14 and provides a delivery apparatus 89.

In order to provide a cell-friendly surface or surfaces on the sleeves 27 and 81, at least one surface of the outer and inner surfaces and preferably both inner and outer surfaces are treated in the manner described in co-pending application Ser. No. 09/385,692 filed Aug. 30, 1999. Thus the surface of the polymer can be characterized as having applied thereto a bioactive coating which is cell friendly and which enhances growth of cells thereon. As described therein, a low temperature plasma-deposited layer is provided on the surface of the polymer to functionalize the surface and provide free amine groups thereon. A spacer/linker molecular layer is covalently bonded to the plasma-deposited layer. A peptide coating such as P15 (Gly-Thr-Pro-Gly-Pro-Gln-Gly-Ile-Ala-Gly-Gln-Arg-Gly-Val-Val; SEQ ID NO: 1) is deposited on the spacer/linker layer. By way of example, the outer surface of the sleeve 27 can be treated first. Thereafter, the sleeve 27 can be inverted by turning it inside out and treating the inside surface which is now outside. Alternatively, both the outside and inside surfaces can be treated at the same time.

Operation and use of the composite expandable devices 11 and 71 with the delivery apparatus 12 and delivery apparatus 89 may now be briefly described as follows. In this connection let it be assumed that a human heart 101 as shown in FIG. 6 has previously had a coronary artery 102 in which there had been formed therein a substantially total occlusion 103. Also let it be assumed that it was found necessary to perform a bypass operation and to insert a saphenous vein graft utilizing a length of saphenous vein 106 which has one end connected into the aorta 107 of the heart by a proximal anastomosis 108 for a blood supply and bypassing the coronary artery occlusion 103 and making a connection to the coronary artery 102 at a distal anastomosis 109. Now let it be assumed that after a period of time there has been a build-up of plaque forming a stenosis in the saphenous vein graft 106 in the region near the distal anastomosis 109.

With such a condition, it is desirable to first use a tapered composite expandable device 71, delivering the same by the use of the tapered balloon 86 of the delivery apparatus 89 on a guide wire in a conventional manner through the femoral artery into the aorta, then through the proximal anastomosis 108 and then advanced into a region adjacent the distal anastomosis 109. The distal tapered balloon 86 is then expanded to expand the device 71 into engagement with the wall of the saphenous vein graft and to thereby enlarge the opening through the saphenous vein graft to enhance blood flow therethrough, through the flow passage formed by the device 71. Thereafter, the tapered balloon 86 and the delivery apparatus 89 is removed.

Let it be assumed that the tapered device 71 has an inadequate length to treat the entire stenosis and it is desired to place another composite expandable device as for example the device 11 (FIG. 1) in tandem or in series with the device 71. Assuming that the guide wire is in place that was used for deploying the first device 71, the shaft 14 of the delivery apparatus 12 can be threaded over the guide wire 18 and a balloon with a composite expandable device 11 mounted thereon advanced into the saphenous vein graft 106 until the distal extremity of the device 11 meets within the proximal larger end 77 of the device 71. The distal extremity can be docked into the open proximal end of the device 71. Thereafter, the balloon 13 can be expanded to complete the docking of the distal extremity of the device 11 in the proximal extremity of the device 71 so that they are deployed in the saphenous vein graft 106 in tandem. The balloon 13 then can be deflated and removed with the delivery apparatus 12 along with the guide wire 18. The positioning of the devices 71 and 11 can be observed fluoroscopically by observing the locations of the radiopaque markers 56 provided on the devices 11 and 71. If the occlusion in the saphenous vein graft is sufficiently long, an additional device 11 can be placed in tandem with the device 11 already in place. If this is desired, the guide wire can be left in place and another balloon delivery apparatus 12 with a device 11 mounted thereon can be advanced into the saphenous vein graft 106 and the distal extremity docked into the expanded proximal extremity of the already positioned device 11. The balloon 13 can be deflated and then removed along with the guide wire 18 and the femoral artery closed in an appropriate manner.

From the foregoing it can be seen that the balloon expandable devices 11 and 71 form a vascular prosthesis which has mechanical and biomedical properties which re-establish and mimic the composition of the biological function and environment of a healthy natural vessel as for example a recently transplanted saphenous vein graft. The support frame for the polymer sleeve is designed to provide adequate support for the polymer sleeve while still providing appropriate compliance corresponding to that of the vessel in which it is disposed. The device with its free outer ends is capable of firmly engaging the wall of the vessel in which it is disposed to ensure that the device remains in place in the desired position within the vessel after deployment. By the use of cylindrical and tapered devices, it is possible to construct a vascular prosthesis which corresponds to the natural geometry of the vessel. The delivery apparatus has a low profile which by utilizing a balloon having an intermediate working portion of a lesser diameter retains this low profile even when the composite expandable device is mounted thereon to facilitate positioning and deployment of the device to the site. Use of the polymer sleeve in the device prevents plaque or deposits within the blood vessel as for example a saphenous vein graft from oozing through the interstices of the frame so that there is unimpeded blood flow through the expanded frame. By covering the polymer sleeve with a peptide such as P15, endothelial cell growth is stimulated. In this way, it is possible to repave the vessel with endothelial cells, nature's most blood compatible surface, and help prevent further spread or degradation of the lumen in the vessel at that site. The construction of the device permitting axial bending makes it possible for the expanded device to readily flex with the vessel.

What is claimed:

1. A composite expandable device for delivery into a vessel carrying blood comprising an expandable support frame having first and second end portions, an impervious polymer sleeve extending over the support frame and having inner and outer surfaces, and a coating disposed on and attached to at least one of the inner and outer surfaces of the polymer sleeve for enhancing endothelial cell growth on the polymer sleeve.

2. A device as in claim 1 wherein both the inner and outer surfaces of the polymer are coated with the coating.

3. A device as in claim 1 wherein the first and second end portions are exposed and free of the sleeve.

4. A device as in claim 1 wherein said expandable support frame and polymer sleeve are cylindrical.

5. A device as in claim 1 wherein said expandable support frame and polymer sleeve are tapered.

6. A device as in claim 1 wherein said expandable support frame is constructed to maintain its length during expansion of the frame.

7. A device as in claim 1 wherein said expandable support frame includes a plurality of axially aligned belts and first and second end portions, each of said belts comprising a plurality of circumferentially spaced struts having first and second ends and foldable links secured to the first and second ends of the struts and interconnecting means serially interconnecting the belts and the first and second end portions to extend along an axis and permitting axial bending between the belts and the end portions while maintaining the length of the device.

8. A device as in claim 7 wherein said interconnecting means includes at least one strut and a plurality of S-shaped links.

9. A device as in claim 7 wherein said interconnecting means between adjacent belts are offset angularly with respect to each other.

10. A device as in claim 9 wherein said end portions are sinusoidal.

11. A device as in claim 7 further including radiopaque markers carried by the end portions.

12. A device as in claim 1 wherein said sleeve is provided with a fold and further including means for securing said frame to said sleeve to inhibit dislodging of the sleeve from the frame during deployment of the device.

13. A device as in claim 1 wherein said coating is the amino acid sequence presented as SEQ ID NO: 1.

* * * * *